United States Patent
Ushiguchi et al.

(10) Patent No.: US 7,094,734 B2
(45) Date of Patent: Aug. 22, 2006

(54) GRANULAR HERBICIDE

(75) Inventors: Yoshio Ushiguchi, Nagano (JP);
Yohichi Hori, Nagano (JP); Katsuhiro Takahashi, Nagano (JP); Shinichi Yamamoto, Kawasaki (JP)

(73) Assignee: Kyoyu Agri Co., Ltd., Kawasaki (JP)

( * ) Notice: Subject to any disclaimer, the term of this patent is extended or adjusted under 35 U.S.C. 154(b) by 140 days.

(21) Appl. No.: 10/483,718

(22) PCT Filed: Jul. 12, 2002

(86) PCT No.: PCT/JP02/07098

§ 371 (c)(1),
(2), (4) Date: Jan. 14, 2004

(87) PCT Pub. No.: WO03/007713

PCT Pub. Date: Jan. 30, 2003

(65) Prior Publication Data

US 2004/0147402 A1    Jul. 29, 2004

(30) Foreign Application Priority Data

Jul. 17, 2001  (JP)  ............ 2001-216682
Apr. 26, 2002  (JP)  ............ 2002-125848

(51) Int. Cl.
A01N 25/12    (2006.01)
A01N 43/40    (2006.01)
A01N 43/58    (2006.01)
A01N 57/02    (2006.01)
A01P 13/00    (2006.01)

(52) U.S. Cl. .............. 504/206; 504/236; 504/250; 504/367

(58) Field of Classification Search ............... 504/206, 504/236, 250, 367
See application file for complete search history.

(56) References Cited

U.S. PATENT DOCUMENTS

| 5,372,989 | A |   | 12/1994 | Geigle et al. |         |
|-----------|---|---|---------|---------------|---------|
| 5,612,285 | A |   | 3/1997  | Arnold        |         |
| 5,693,593 | A |   | 12/1997 | Arnold        |         |
| 5,994,271 | A |   | 11/1999 | Ravetta et al.|         |
| 6,051,533 | A | * | 4/2000  | Kajikawa et al. | 504/206 |

FOREIGN PATENT DOCUMENTS

| EP | 0 273 551 | 7/1988 |
| EP | 0 394 211 | 10/1990 |
| EP | 0 413 267 | 2/1991 |
| EP | 0 582 561 | 2/1994 |
| JP | 61-286302 | 12/1986 |
| JP | 6-256121  | 9/1994 |
| JP | 11-255609 | 9/1999 |
| WO | 94/10844  | 5/1994 |
| WO | 97/02742  | 1/1997 |
| WO | 01/08492  | 2/2001 |

* cited by examiner

*Primary Examiner*—S. Mark Clardy
(74) *Attorney, Agent, or Firm*—Wenderoth, Lind & Ponack, L.L.P.

(57) ABSTRACT

This invention provides a granular herbicide for direct foliage application to undesirable plants, which contains a water soluble, non-selective foliage-application type herbicidally active compound as the active ingredient, having an average granule size within a range of 0.21–1 mm and an elution ratio of said active ingredient of at least 20% when 20 mg of the granular herbicide is treated with a circular filter paper sheet of 55 mm in diameter which is impregnated with 50 μl of water.

9 Claims, No Drawings

GRANULAR HERBICIDE

TECHNICAL FIELD

This invention relates to a granular herbicide for foliage application directly onto undesirable plants, which contains a water soluble, non-selective foliage application type herbicidally active compound such as glyphosate; and to a process for killing or controlling undesirable plants using said herbicide.

BACKGROUND ART

Non-selective foliage application type herbicidally active compounds such as glyphosate kill or control many species of weeds non-selectively, and hence have been used in non-agricultural land such as railways, created land, parking lots, parks and house circumferences. Furthermore, because said herbicidally active compounds falling on soil surface lose their herbicidal activity against plants after they are adsorbed in the soil and exhibit no phytotoxicity for useful plants, they are widely used also in agricultural land such as orchard, vegetable gardens and paddy fields before ploughing. Conventionally, for uniformly applying such a non-selective foliage application type herbicidal compound as glyphosate to allow exhibition of its maximum effect, generally such a non-selective foliage application type herbicidally active compound is formulated into such preparation forms as liquid, water soluble granule, flowable, wettable powder and the like, and a method of diluting said preparation forms with water is adopted.

These preparations, however, are difficult for use where water facilities are bad because they are used as diluted with water. Moreover, for spraying these preparations, suitable devices such as a sprayer is indispensable. Besides such problems, their application with a sprayer scatters fine spray particles which are apt to be drifted with wind. Therefore, their spray in the vicinities of useful plants or to the areas close to plant bases is liable to cause phytotoxicity, and is normally avoided.

On the other hand, recently water soluble granule or water dispersible granule preparations are developed in consideration of the problems incidental to disposal of containers and toxicity of solvents used in emulsifiable concentrate, and also for such reasons as their better flowability and easier measurement compared with water soluble powder or wettable powder preparations. Furthermore, they do not cause dust scattering in the occasions of preparing spraying liquids therefrom, exhibiting improved safety for the workers. As water soluble granule or water dispersible granule preparations containing glyphosate as herbicidally active ingredient, for example, water dispersible granule preparations comprising glyphosate and polyglycolether nonionic surfactant having a wax viscosity [JP Hei 6 (1994)-256121A] or water soluble granule preparations comprising glyphosate, a surfactant and polyalkylene glycol as an extrusion granulating assistant [JP Hei 11 (1999)-255609A] have been proposed. These water soluble granule or water dispersible granule preparations, however, are invariably to be diluted with water before application, like liquid, emulsifiable concentrate or flowable preparations and the problems as above-described still remain unsolved.

DISCLOSURE OF THE INVENTION

We have engaged in concentrative studies with the view to solve above problems to discover: surprisingly, when water soluble, non-selective foliage application type herbicidally active compounds such as glyphosate are formulated into small size granular preparations which contain said herbicidally active compounds in a state allowing quick elution thereof, and directly applied to weeds as they are, the granular preparations are effectively deposited and retained on foliage of the weeds and readily eluted with minor amounts of water such as the night dew or morning dew to accomplish fully satisfactory herbicidal effect, whereby solving all of the problems of water facilities, spraying equipment, drifting with wind, etc. at once. The present invention is whereupon completed.

Thus, the present invention provides a granular herbicide for direct foliage application to undesirable plants, which contains a water soluble, non-selective foliage application type herbicidally active compound as the active ingredient, characterized by having an average granule size within a range of 0.21–1 mm and an elution ratio of said active ingredient of at least 20% when 20 mg of the granular herbicide is treated with a circular filter paper sheet of 55 mm in diameter which is impregnated with 50 µl of water.

The present invention also provides a method of killing or controlling undesirable plants, characterized by directly applying said granular herbicide onto foliage of undesirable plants.

Hereinafter the granular herbicide and the method of its use of the present invention are explained in further detail.

EMBODIMENTS OF THE INVENTION

The herbicidally active compound which is used as the active ingredient in the granular herbicide of the present invention is water soluble and is of a type to be absorbed through plant foliage to kill or control the plants non-selectively. The compound suitably has solubility in water of at least 10 g/liter at 20° C. Said herbicidally active compound desirably is such that its herbicidal activity is substantially lost when it drops on soil surface and is adsorbed into the soil. As specific examples of this type of herbicidal compound (which may hereafter be referred to as "herbicidal ingredient of the present invention"), glyphosate or salts thereof (e.g., sodium salts, ammonium salts, isopropylamine salts, trimesium salts and the like), bialaphos, glufosinate, diquat, paraquat and the like can be named, the herbicidal ingredient of the present invention not being limited to the above-named. Of these, particularly glyphosate and salts thereof are preferred.

According to the invention, these granular herbicides are formulated into such a granular preparation form having an average granule size within a range of 0.21–1 mm, preferably 0.3–0.8 mm, inter alia, 0.5–0.8 mm and an elution ratio of the herbicidal ingredient of the present invention from the preparation as measured by the following method of at least 20%, preferably at least 40%, inter alia, at least 50%.

<Method for Measuring Elution Ratio of Herbicidal Ingredient of the Present Invention>

Fifty (50) µl distilled water is weighed with a micropipette and dropped on the central area of a circular filter paper sheet of 55 mm in diameter (ADVANTEC Co., No.5C). At the time the water has diffused and infiltrated over the entiety of the filter paper (in about 2 minutes), accurately weighed 20 mg of a sample preparation is dispersed on the filter paper, taking care that the granules shall not overlap with each other.

The filter paper on which the sample preparation is dispersed is immediately put in a desiccator containing water at its bottom portion and left there for an hour. The filter paper is withdrawn from the desiccator, mildly patted to remove the preparation remaining thereon and thereafter extracted with 10 ml of distilled water. The herbicidal ingredient of the present invention contained in the extracted solution is determined by high performance liquid chromatography (HPLC analysis), and from the determined value the eluted amount a mg of the herbicidal ingredient per mg of the sample preparation is decided.

Separately, accurately weighed 20 mg of a sample preparation is dispersed in 10 ml of distilled water to cause complete elution of the herbicidal ingredient of the present invention in the sample preparation into the water which then is centrifuged. The supernatant is given an HPLC analysis to determine the herbicidal ingredient contained in the supernatant, and from the determined value the amount b mg of the herbicidal ingredient contained per mg of the sample preparation is decided.

The elution ratio(%) of the herbicidal ingredient of the present invention from the sample preparation is calculated by a formula, $$a/b \times 100.$$

Granular herbicides of the present invention can be adjusted of their average granule size to fall within a range of 1.0 mm–0.21 mm, by means of combined selection of a screen diameter of the granulating machine used (between 1.0 mm–0.2 mm) and mesh size of the sieve used (between 1.0 mm–0.21 mm).

Granular herbicides of the present invention having the specified average granule size and the specified elution ratio of herbicidal ingredient of the present invention can be formulated following accepted formulation methods of water dispersible granule preparations, for example, by granulating one or more of the herbicidal ingredients of the present invention together with surfactants, binders and carriers, and further with polyhydric alcohols where necessary.

Surfactants useful for formulating granular herbicides of the present invention are subject to no specific limitation, and for example, any of anionic surfactants such as alkylbenzenesulfonate, alkylnaphthalenesulfonate, naphthalenesulfonate-formaline condensate, dialkylsulfosuccinate, lignin sulfonate, $\alpha$-olefin sulfonate, alkane sulfonate, polystyrene sulfonate, alkyl ether sulfate salt, polyoxyethylene alkyl ether sulfate salt, polyoxyethylene alkylphenyl ether sulfate salt, polyoxyethylene polystyrylphenyl ether sulfate-salt, polyoxyethylene alkyl ether phosphate salt, polyoxyethylene alkyl phenyl ether phosphate salt, polyoxyethylene polystyryl phenyl ether phosphate salt, fatty acid salt, isobutylene-maleic acid copolymer salt, styrene-maleic acid copolymer salt, polyacrylic acid salt and the like; nonionic surfactants such as silicone-type surfactants, polyoxyethylene alkyl ether, polyoxyethylene alkyl phenyl ether, polyoxyethylenestyrylphenyl ether, polyoxyethylenestyrylphenyl ether polymer, polyoxyethylenesorbitan alkyl ester, polyoxyethylene polyoxypropylene block polymer, polyoxyethylene alkyl ester, polyoxyethylene alkylamine and the like; and cationic surfactants such as alkylamine salt, tetraalkylammonium salt, trialkylbenzylammonium salt and the like can be named. Furthermore, ampholytic surfactants or the like may be used, where necessary. These surfactants can be used either singly or in combination of two or more. The use rate of these surfactants is not critical, and from such considerations as the effect and economy, generally their use within a range of 0.1–30% by weight, in particular, 2–10% by weight, to the total amount of the preparation is desirable.

Binders useful for formulating the granular herbicides of the present invention is again subject to no particular limitation. For example, starch, hydrogenated starch hydrolysate, dextrin, cellulose, methyl cellulose, ethyl cellulose, carboxymethyl cellulose, hydroxyethyl cellulose, hydroxypropyl cellulose, carboxymethyl starch, pullulan, sodium alginate, ammonium alginate, alginic acid propylene glycol ester, guar gum, locust bean gum, gum arabi, xanthane gum, gelatine, casein, polyvinyl alcohol, polyethylene oxide, polyethylene glycol, ethylene/propylene block polymer, sodium polyacrylate, polyvinylpyrrolidone and the like can be named. These binders can be used either singly or in combination of two or more. While the use rate of these binders is subject to no specific limitation, generally their use within a range of 0.1–40% by weight, in particular, 2–10% by weight, to the total amount of the preparation is desirable from the standpoints of effect and economy.

Carriers useful for formulating the granular herbicides of the present invention may be either inorganic or organic carriers, and are subject to no specific limitation, examples of inorganic carriers including clay, bentonite, talc, calcium carbonate, sodium carbonate, zeeklite, sericite, acid clay, quartzite, diatomaceous silica, pumice, zeolite, vermiculite, potassium chloride, urea, white carbon, ammonium sulfate, sodium sulfate, perlite, magnesium sulfate, attapulgite and the like; and examples of organic carriers including glucose, maltose, sucrose, lactose and the like. These inorganic or organic carriers can be used singly, or two or more of these inorganic carriers and/or organic carriers may be concurrently used.

Furthermore, polyhydric alcohols which can be optionally used for formulating the granular herbicides of the present invention are subject to no specific limitation, examples of which including glycerine, ethylene glycol, diethylene glycol, propylene glycol, hexylene glycol, polyethylene glycol, polypropylene glycol, xylitol, maltitol, butylene glycol, polyoxyethylene methyl glycoside, mannitol, sorbitol and the like. The use rate of these polyhydric alcohols is not critical, but generally their use within a range of 0.1–40% by weight, in particular, 2–20% by weight, to the total amount of the preparation is desirable from the standpoints of effect and economy.

Formulation method of granular herbicides of the present invention is subject to no specific limitation so long as the requirements for the average granule size and the elution ratio of herbicidal ingredient of the present invention are satisfied. Normally, however, the formulation can be carried out, for example, by the following methods: the herbicidal ingredient of the present invention is mixed with surfactants, binders and carriers, and further optionally with polyhydric alcohols; then 1) the mixture is kneaded with addition of water, granulated with an extrusion granulating machine, adjusted of the granule size, dried and sieved; 2) the mixture is granulated with a tumbling granulating machine under addition of water, adjusted of the granule size, dried and sieved; 3) the mixture is dispersed in water, granulated with a spray granulating machine, adjusted of the granule size, dried and sieved; or 4) onto a flowing mixture of surfactants and carriers, the herbicidally active ingredient and a binder solution are sprayed and granulated with a fluidized bed granulating machine, adjusted of the granule size, dried and sieved. The sieving can be carried out using sieves with mesh sizes between 1.0 mm and 0.21 mm in combination.

The adjustment of the elution ratio of herbicidal ingredient of the present invention from so formulated preparation can be conducted with ease, by adjusting the use rate of the surfactants and/or binders.

Content of the herbicidal ingredient of the present invention in so formulated granular herbicide of the present invention is not strictly limited, and may be varied according to the kind of the herbicidal ingredient used. Generally, however, the content preferably lies within a range of 0.01–90% by weight, in particular, 0.1–60% by weight, inter alia, 2–25% by weight, to the total amount of the preparation.

The granular herbicides provided by the present invention are applicable directly to foliage of undesirable plants, retaining their granular preparation form, without being diluted with water like conventional herbicides. The application can be done by scattering the granular herbicidal preparation as it is, either by hand or from its container directly over plant foliage, or at a place like a large field, it is also permissible to use an application tool like a granule applicator for direct application of the preparation onto plant foliage.

The direct application causes the granular herbicide of the present invention to fall and be deposited on foliage of undesirable plants, and from the herbicide its herbicidal ingredient is readily eluted with such miner amount of moisture like night dew or morning dew (in certain cases the herbicide granules are readily collapsed and dispersed to allow elution of the herbicidal ingredient). The eluted herbicidal ingredient is absorbed by the plant foliage, to exhibit excellent herbicidal effect as well as applying conventional wettable powder or liquid preparations after dilution with water.

The granular herbicidal preparations of the present invention can be applied, for example, to industrial parks, shoulders or slopes of railroad or driveway, orchards (e.g., vineyard, orange orchard and the like), tea gardens, forest lands, playgrounds, well-wooded gardens and the like, to control undesirable plant species present in such areas. The application rate of the granular herbicidal preparation of the present invention in such occasions is variable over a broad range depending on the kind of the herbicidal ingredient, the species of plants to kill or control, and percentage of vegetational cover. Whereas, generally suitable application rate ranges 50 g/a–2000 g/a, in particular, 150 g/a–300 g/a.

Application of the granular herbicide of the present invention is preferably carried out on a windless or faintly windy day. It is also more effective to carry it out in the evening when night dew or morning dew are apt to fall.

EXAMPLES

Hereinafter the invention is explained more specifically, referring to working examples, it being understood that the invention is not limited to these examples.

Example 1

Glyphosate isopropylamine salt 21 wt %, polyoxyethylenestyryl-phenyl ether 10 wt %, starch 10 wt % and diatomaceous silica 59 wt % were measured into a mixing vessel and mixed for 5 minutes with a universal mixer. Thirty (30) wt % of water per 100 wt % of this mixture was added and together kneaded for further 5 minutes. The kneaded product was granulated with a basket type granulating machine equipped with a 0.8 mm mesh size screen (Hata Ironworks Co.). The size-adjusted granules obtained were dried and then sifted (1.0–0.21 mm) to provide a granular herbicidal preparation (Example-1).

Example 2

Glyphosate isopropylamine salt 21 wt %, dialkylsulfosuccinate 10 wt %, sodium polyacrylate 2 wt % and diatomaceous silica 67 wt % were measured into a mixing vessel and mixed for 5 minutes with a universal mixer. Thirty (30) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Example-2).

Example 3

Glyphosate isopropylamine salt 21 wt %, dialkylsulfosuccinate 10 wt %, sodium polyacrylate 2 wt % and diatomaceous silica 67 wt % were measured into a mixing vessel and mixed for 5 minutes with a universal mixer. Thirty (30) wt % of water per 100 wt % of this mixture was added and together kneaded for further 5 minutes. The kneaded product was granulated with a basket type granulating machine equipped with a 0.5 mm mesh size screen (Hata Ironworks Co.). So obtained size-adjusted granules were dried and sifted (1.0–0.21 mm) to provide a granular herbicidal preparation (Example-3).

Example 4

Glyphosate isopropylamine salt 21 wt %, dialkylsulfosuccinate 6 wt %, polyoxyethylene alkyl ether 4 wt %, sodium polyacrylate 2 wt %, diatomaceous silica 57 wt % and bentonite 10 wt % were measured into a mixing vessel and mixed for 5 minutes with a universal mixer. Twenty-four (24) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Example-4).

Example 5

Glyphosate isopropylamine salt 7 wt %, dialkylsulfosuccinate 6 wt %, polyoxyethylene alkyl ether 4 wt %, sodium polyacrylate 2 wt %, diatomaceous silica 71 wt % and bentonite 10 wt % were measured into a mixing vessel and mixed for 5 minutes with a universal mixer. Thirty (30) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Example-5).

Example 6

Glufosinate 10 wt %, alkylamine salt 10 wt %, carboxymethyl cellulose 2 wt %, diatomaceous silica 68 wt % and bentonite 10 wt % were measured into a mixing vessel and mixed for 5 minutes with a universal mixer. Twenty-four (24) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Example-6).

Example 7

Bialaphos 10 wt %, dialkylsulfosuccinate 10 wt %, sodium polyacrylate 2 wt %, diatomaceous silica 68 wt % and bentonite 10 wt % were measured into a mixing vessel and mixed for 5 minutes with a universal mixer. Twenty-four (24) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Example-7).

Example 8

Glyphosate isopropylamine salt 21 wt %, dialkylsulfosuccinate 10 wt %, glycerine 15 wt %, sodium polyacrylate 2 wt % and diatomaceous silica 52 wt % were measured into a mixing vessel and mixed for 5 minutes with a universal mixer. Twenty (20) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.3 mm) to provide a granular herbicidal preparation (Example-8).

Example 9

Glyphosate isopropylamine salt 7 wt %, dialkylsulfosuccinate 6 wt %, polyoxyethylene alkyl ether 4 wt %, sodium polyacrylate 2 wt %, glycerine 15 wt %, diatomaceous silica 56 wt % and bentonite 10 wt % were measured into a mixing vessel and mixed for 5 minutes with a universal mixer. Twenty (20) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.3 mm) to provide a granular herbicidal preparation (Example-9).

Comparative Example 1

Glyphosate isopropylamine salt 25 wt %, sodium ligninsulfonate 5 wt %, sodium dodecylbenzenesulfonate 0.3 wt %, white carbon 34 wt %, talc 18.7 wt % and bentonite 17 wt % were measured into a mixing vessel and mixed for 5 minutes with a universal mixer. Fifty-five (55) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Comparative Example-1).

Comparative Example 2

Glyphosate isopropylamine salt 25 wt %, isobutylene-maleic acid copolymer 2 wt %, alkylbenzenesulfonate 10 wt %, carboxymethyl cellulose 5 wt %, perlite 45 wt % and clay 13 wt % were measured into a mixing vessel and mixed for 5 minutes with a universal mixer. Thirty-six (36) wt % of water per 100 wt % of this mixture was added and together kneaded for further 5 minutes. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Comparative Example-2).

Comparative Example 3

Glyphosate isopropylamine salt 25 wt %, alkylbenzenesulfonate 10 wt %, silicone-type surfactant 6 wt %, carboxymethyl cellulose 2 wt %, diatomaceous silica 40 wt % and clay 17 wt % were measured into a mixing vessel and mixed for 5 minutes with a universal mixer. The kneaded product was granulated with a basket type granulating machine equipped with a 0.8 mm mesh size screen (Hata Ironworks Co.). So obtained size-adjusted granules were dried and sifted (1.0–0.21 mm) to provide a granular herbicidal preparation (Comparative Example-3).

Comparative Example 4

Glyphosate isopropylamine salt 21 wt %, dialkylsulfosuccinate 10 wt %, sodium polyacrylate 2 wt % and diatomaceous silica 67 wt % were measured into a mixing vessel and mixed for 5 minutes with a universal mixer. Thirty (30) wt % of water per 100 wt % of this mixture was added and together kneaded for further 5 minutes. The kneaded product was granulated with a basket type granulating machine equipped with a 1.5 mm mesh size screen (Hata Ironworks Co.). So obtained size-adjusted granules were dried and sifted (1.68–1 mm) to provide a granular herbicidal preparation (Comparative Example-4).

Comparative Example 5

KUMIAI KUSA TOBAN™ manufactured by Kumiai Chemical Industry Co. Ltd. (a glyphosate ammonium salt water soluble granule, containing 20% of glyphosate ammonium salt) (Comparative Example-5) was used in its sold form.

Comparative Example 6

KARUNAKUSU™ manufactured by Yashima Chemical Industry Co., Ltd. (a glyphosate isopropylamine salt liquid preparation containing 41.0% of glyphosate isopropylamine salt) (Comparative Example-6) was used in its sold form.

Comparative Example 7

BASTA (Liquid)™ manufactured by Nissan Chemical Industries, Ltd. (a glufosinate liquid preparation containing 18.5% of glufosinate) (Comparative Example-7) was used in its sold form.

Comparative Example 8

HERBY (Liquid)™ manufactured by Hokko Chemical Industry Co., Ltd. (a bialaphos liquid preparation containing 18% of bialaphos) (Comparative Example-8) was used in its sold form.

Elution ratios of herbicidally active ingredients from the granular herbicides as obtained in above Examples 1–9 and Comparative Examples 1–4; the water soluble granule preparation of Comparative Example 5, were measured by the earlier described method. The result was as shown in the following Table 1.

Test Example 1 (Elutability test)

TABLE 1

| No. | Elution ratio (%) |
|---|---|
| Example | |
| 1 | 48 |
| 2 | 60 |
| 3 | 68 |
| 4 | 55 |
| 5 | 61 |
| 6 | 56 |
| 7 | 60 |
| 8 | 65 |
| 9 | 66 |
| Comparative Example | |
| 1 | 0 |
| 2 | 9 |
| 3 | 14 |
| 4 | 58 |
| 5 | 6 |

Using the granular herbicides obtained in above Example 1–9 and Comparative Examples 1–4; the water soluble granule preparation of Comparative Example 5; and the herbicidal liquid preparations of Comparative Examples 6–8, their herbicidal effect was evaluated.

Test Example 2 (Pot Test)

Pots of each 1/3000 a scale were filled with upland soil and onto which seeds of southern crabgrass [*Digitaria ciliaris* (*Retz.*) *Koeler*], slender amaranthus [*Amaranthus viridis L.*] and common lambsquarters [*Chenopodium album L.*] were planted, covered up with the soil, and after the crabgrass grew to about 20–30 cm in height, the granular herbicides of Examples 1–9 and Comparative Examples 1–4, the water soluble granule preparation of Comparative Example 5 and the herbicidal liquid preparations of Comparative Examples 6–8 were applied.

The modes of application were as follows: the granular herbicides of Examples 1–9 and Comparative Examples 1–4 were hand-scattered as they were, not being diluted with water; each prescribed amount of the herbicidal liquid preparations of Comparative Examples 6–8 were diluted with 10 liters/a of water and applied with a hand sprayer; and the water soluble granule preparation of Comparative Example 5 was applied in two ways, i.e., either hand-scattered as it was, without being diluted, or a prescribed amount thereof was diluted with 10 liters/a of water and applied with a hand-sprayer. Onto the sections where the granular herbicides of Examples 1–9 and Comparative Examples 1–4, and the water soluble granule preparation of Comparative Example 5 were applied by hand, water was lightly sprinkled with a hand-spryer in advance of the herbicide application. The test was conducted in four replicates.

Four weeks after the application, herbicidal effect was evaluated based on the following ratings. The results were as given in the following Table 2.

| Evaluation standard | | |
|---|---|---|
| 5 | kill or control ratio | at least 90% |
| 4 | kill or control ratio | 70–90% |
| 3 | kill or control ratio | 40–70% |
| 2 | kill or control ratio | 20–40% |
| 1 | kill or control ratio | 5–20% |
| 0 | kill or control ratio | 5% or less |

TABLE 2

| Chemical preparation | Application rate (g, ml/a) | Application rate of active ingredient (gai/a) | Dilution with water | Herbicidal effect southern crabgrass | slender amaranthus | common lambsquarters |
|---|---|---|---|---|---|---|
| Example-1 | 97.6 | 20.5 | No | 5 | 5 | 5 |
| Example-2 | 97.6 | 20.5 | No | 5 | 5 | 5 |
| Example-3 | 97.6 | 20.5 | No | 5 | 5 | 5 |
| Example-4 | 97.6 | 20.5 | No | 5 | 5 | 5 |
| Example-5 | 292.8 | 20.5 | No | 5 | 5 | 5 |
| Example-6 | 92.5 | 9.25 | No | 5 | 5 | 5 |
| Example-7 | 90.0 | 9.0 | No | 5 | 5 | 5 |
| Example-8 | 97.6 | 20.5 | No | 5 | 5 | 5 |
| Example-9 | 292.8 | 20.5 | No | 5 | 5 | 5 |
| Comparative Example-1 | 82.0 | 20.5 | No | 0 | 0 | 0 |
| Comparative Example-2 | 82.0 | 20.5 | No | 0 | 1 | 0 |
| Comparative Example-3 | 82.0 | 20.5 | No | 1 | 2 | 1 |
| Comparative Example-4 | 97.6 | 20.5 | No | 0 | 0 | 0 |
| Comparative Example-5 | 102.5 | 20.5 | No | 1 | 1 | 1 |
| | | | Yes | 5 | 5 | 5 |
| Comparative Example-6 | 50.0 | 20.5 | Yes | 5 | 5 | 5 |

TABLE 2-continued

| Chemical preparation | Application rate (g, ml/a) | Application rate of active ingredient (gai/a) | Dilution with water | Herbicidal effect | | |
|---|---|---|---|---|---|---|
| | | | | southern crabgrass | slender amaranthus | common lambsquarters |
| Comparative Example-7 | 50.0 | 9.25 | Yes | 5 | 5 | 5 |
| Comparative Example-8 | 50.0 | 9.0 | Yes | 5 | 5 | 5 |

Test Example 3 (Field Test)

Mowing a simple community of southern crabgrass (percentage of vegetational cover: 90–98%) in the orchard of a laboratory, the granular herbicides of Examples 1–9 and Comparative Examples 1–4, the water soluble granule preparation of Comparative Example 5 and the herbicidal liquid preparations of Comparative Examples 6–8 were applied when the regrown crabgrass reached 15–20 cm in height.

The modes of application were as follows: the granular herbicides of Examples 1–9 and Comparative Examples 1–4 were hand-scattered as they were, not being diluted with water; each prescribed amount of the herbicidal liquid preparations of Comparative Examples 6–8 were diluted with 10 liters/a of water and applied with a hand sprayer; and the water soluble granule preparation of Comparative Example 5 was applied in two ways, i.e., either hand-scattered as it was, without being diluted, or a prescribed amount thereof was diluted with 10 liters/a of water and applied with a hand sprayer.

The test was conducted in two replicates, over the areas of 1 m² each. The applications were performed under the condition that morning dew was no more present so that moisture supply would come from the morning dew falling on the next day.

After four weeks of the application, the herbicidal effect was evaluated based on the same rating standard as used in Test Example 2. The results were as given in the following Table 3.

TABLE 3

| Chemical preparation | Application rate (g, ml/a) | Application rate of active ingredient (gai/a) | Dilution with water | Herbicidal effect Southern crabgrass |
|---|---|---|---|---|
| Example-1 | 97.6 | 20.5 | No | 5 |
| Example-2 | 97.6 | 20.5 | No | 5 |
| Example-3 | 97.6 | 20.5 | No | 5 |
| Example-4 | 97.6 | 20.5 | No | 5 |
| Example-5 | 292.8 | 20.5 | No | 5 |
| Example-6 | 92.5 | 9.25 | No | 5 |
| Example-7 | 90.0 | 9.0 | No | 5 |
| Example-8 | 97.6 | 20.5 | No | 5 |
| Example-9 | 292.8 | 20.5 | No | 5 |
| Comparative Example-1 | 82.0 | 20.5 | No | 0 |
| Comparative Example-2 | 82.0 | 20.5 | No | 0 |
| Comparative Example-3 | 82.0 | 20.5 | No | 1 |
| Comparative Example-4 | 97.6 | 20.5 | No | 0 |

TABLE 3-continued

| Chemical preparation | Application rate (g, ml/a) | Application rate of active ingredient (gai/a) | Dilution with water | Herbicidal effect Southern crabgrass |
|---|---|---|---|---|
| Comparative Example-5 | 102.5 | 20.5 | No | 0 |
| | | | Yes | 5 |
| Comparative Example-6 | 50.0 | 20.5 | Yes | 5 |
| Comparative Example-7 | 50.0 | 9.25 | Yes | 5 |
| Comparative Example-8 | 50.0 | 9.0 | Yes | 5 |

Effect of the Invention

As clearly demonstrated by the above test results, these granular herbicides of the present invention, which are imparted with the property of giving an elution ratio of the herbicidally active ingredient of at least 20% when 20 mg of a tested herbicide is treated with a circular filter paper sheet of 55 mm in diameter which is impregnated with 50 μl of water, exhibit the intended effect when directly applied onto foliage of weeds as they are, without being diluted with water, through the mechanism that the active ingredient in the granular herbicides which fell and were deposited on the weed foliage is readily eluted with water of about a quantity supplied by morning dew or more and absorbed by the weed foliage. Furthermore, the granular herbicides of the present invention do not require any special application tool or apparatus but can be applied with hand or from their containers directly onto weeds, to achieve equivalent herbicidal effect to the cases of using conventional application method of diluting a liquid preparation with water and applying the same with a sprayer or the like, while avoiding chemical injury on ambient crops caused by drifting.

The invention claimed is:

1. A granular herbicide for direct foliage application to undesirable plants, which contains a water soluble, non-selective foliage-application type herbicidally active compound as the active ingredient, characterized by having an average granule size within a range of 0.21–1 mm and an elution ratio of said active ingredient of at least 20% when 20 mg of the granular herbicide is treated with a circular filter paper sheet of 55 mm in diameter which is impregnated with 50 μl of water.

2. A granular herbicide according to claim 1, in which the water soluble, non-selective foliage-application type herbicidally active compound is at least one compound selected from the group consisting of glyphosate or its salts, bialaphos, glufosinate, diquat and paraquat.

3. A granular herbicide according to claim 1, in which the water soluble, non-selective foliage-application type herbicidally active compound is glyphosate or its salt.

4. A granular herbicide according to claim 1, in which the herbicidally active compound has a water solubility of at least 10 g/liter at 20° C.

5. A granular herbicide according to claim 1, having an average granule size within a range of 0.3–0.8 mm.

6. A granular herbicide according to claim 1, in which the elution ratio of the active ingredient is at least 40%.

7. A granular herbicide according to claim 1, which is obtained by forming the herbicidally active compound into granules, with surfactant(s), binder(s) and carrier(s), and further optionally with polyhydric alcohol(s).

8. A granular herbicide according to claim 1, which contains 0.01–90% by weight, preferably 1–60% by weight, of the herbicidally active compound.

9. Method for killing or controlling undesirable plants, characterized by directly applying the granular herbicide of claim 1 to foliage of undesirable plants.

* * * * *